United States Patent
Mohl (10) Patent No.: US 11,890,192 B2
(45) Date of Patent: Feb. 6, 2024

(54) ANNULOPLASTY DEVICE

(71) Applicant: AVVIE GMBH, Vienna (AT)

(72) Inventor: Werner Mohl, Altenmarkt-Thennenberg (AT)

(73) Assignee: AVVIE GMBH, Vienna (AT)

(\*) Notice: Subject to any disclaimer, the term of this patent is extended or adjusted under 35 U.S.C. 154(b) by 0 days.

(21) Appl. No.: 17/909,676

(22) PCT Filed: Feb. 25, 2021

(86) PCT No.: PCT/IB2021/051570
§ 371 (c)(1),
(2) Date: Sep. 6, 2022

(87) PCT Pub. No.: WO2021/176306
PCT Pub. Date: Sep. 10, 2021

(65) Prior Publication Data
US 2023/0107129 A1    Apr. 6, 2023

(30) Foreign Application Priority Data
Mar. 3, 2020   (EP) .................................... 20020095

(51) Int. Cl.
*A61F 2/24*   (2006.01)

(52) U.S. Cl.
CPC .......... *A61F 2/2445* (2013.01); *A61F 2/2466* (2013.01); *A61F 2210/0014* (2013.01);
(Continued)

(58) Field of Classification Search
CPC ................. A61F 2/2445; A61F 2/2466; A61F 2210/0014; A61F 2220/0016;
(Continued)

(56) References Cited

U.S. PATENT DOCUMENTS

| 2013/0226290 A1 | 8/2013 | Yellin et al. |
| 2018/0042723 A1 | 2/2018 | Yellin et al. |

(Continued)

FOREIGN PATENT DOCUMENTS

| WO | 2005046488 A2 | 5/2005 |
| WO | 2008088716 A1 | 7/2008 |

OTHER PUBLICATIONS

International Search Report and Written Opinion received in PCT/IB2021/051570 dated May 25, 2021, pp. 17.
(Continued)

*Primary Examiner* — Brian A Dukert
*Assistant Examiner* — Rebecca Lynee Zimmerman
(74) *Attorney, Agent, or Firm* — Liang & Hennessey LLP; Brian Hennessey (57) ABSTRACT

The invention relates to an annuloplasty device for use on a posterior annulus of a mitral valve, including at least a first and a second anchor unit, preferably a plurality of anchor units, that are deployable to the mitral valve by means of a vascular delivery device, such as a catheter, and positionable in a row along the annulus, including anchor means arranged on each of the first and second anchor units, wherein the first and second anchor units are interconnected by connection means defining a distance between the first and second anchor units, further including pulling means for reducing the distance between the first and second anchor units so as to pull the annulus together, wherein the anchor units are arranged to be rotatable to one another around a longitudinal axis extending along the row.

16 Claims, 9 Drawing Sheets

(52) U.S. Cl.
CPC ............... *A61F 2220/0016* (2013.01); *A61F 2220/0091* (2013.01); *A61F 2230/0036* (2013.01); *A61F 2250/0006* (2013.01)

(58) Field of Classification Search
CPC ...... A61F 2220/0091; A61F 2230/0036; A61F 2250/0006; A61F 2/2442; A61F 2/2448
See application file for complete search history.

(56) References Cited

U.S. PATENT DOCUMENTS

| | | | |
|---|---|---|---|
| 2018/0140421 A1* | 5/2018 | Sampson | A61F 2/2487 |
| 2018/0154111 A1* | 6/2018 | Nguyen | A61B 17/0401 |
| 2018/0177503 A1* | 6/2018 | Miraki | A61B 17/0487 |

OTHER PUBLICATIONS

International Preliminary Report received in PCT/IB2021/051570 dated Jan. 28, 2022, pp. 6.

* cited by examiner

ANNULOPLASTY DEVICE

CROSS-REFERENCE TO RELATED APPLICATIONS

The present application is a national phase application of PCT Application No. PCT/IB2021/051570, filed Feb. 25, 2021, entitled "ANNULOPLASTY DEVICE", which claims the benefit of European Patent Application No. 20020095.4, filed Mar. 3, 2020, each of which is incorporated by reference in its entirety.

BACKGROUND OF THE INVENTION

1. Field of the Invention

The invention refers to an annuloplasty device for use on a posterior annulus of a mitral valve, comprising at least a first and a second anchor unit, preferably a plurality of anchor units, that are deployable to the mitral valve by means of a vascular delivery device, such as a catheter, and positionable in a row along the annulus, comprising anchor means arranged on each of the first and second anchor units. Furthermore, the invention relates to a delivery device for delivering and deploying the annuloplasty device to the annulus of the mitral valve.

2. Description of the Related Art

The mitral valve is situated in the left heart between the left atrium and the left ventricle. It comprises two leaflets, namely an anterior and a posterior leaflet, which are divided by two commissures, namely an anterolateral and a posteromedial commissure. The anterior leaflet is divided in 3 areas, namely A1, A2 and A3 and the posterior leaflet is divided in three areas, namely P1, P2 and P3. The opening of the mitral valve is surrounded by the mitral annulus, which is a fibrous ring that is attached to the mitral valve leaflets. The mitral annulus is saddle shaped and contracts and reduces its surface area during systole in order to aid complete closure of the leaflets. Pathological expansion of the annulus can result in malcoaptation of the leaflets, i.e. in leaflets that do not close properly, which in turn leads to mitral insufficiency.

Under normal conditions, blood flows through an open mitral valve during diastole with contraction of the left atrium, and the mitral valve closes during systole with contraction of the left ventricle. The valve opens and closes because of the pressure differences prevailing in the heart, i.e. the mitral valve opens when there is greater pressure in the left atrium than in the ventricle, and closes when there is greater pressure in the ventricle than in the atrium.

The mitral annulus changes in shape and size during the cardiac cycle. Due to the contraction of the left atrium surrounding it the mitral annulus is smaller at the end of atrial systole, like a sphincter, which is important for proper coaptation of the leaflets of the mitral valve when the left ventricle contracts and pumps the blood.

Leaking valves can be corrected by mitral valve annuloplasty, which aims at restoring proper leaflet adjustment. Annuloplasty devices are fixed to the annulus, preferably the posterior annulus, of the mitral valve and are normally used to shorten the circumferential length of the pathologically stretched annulus of the mitral valve by 20-30%, which then allows for correct coaptation of the mitral valve.

WO2008/088716A1 discloses an annuloplasty device comprising a support, which exhibits a plurality of anchor units, which are arranged in equal distance to one another, and a tether, which is connected to the support and to the plurality of anchor units, and which is configured to be pulled proximally in order to reduce the circumference of the mitral valve.

The major drawback of the device as disclosed in WO2008/088716A1 is that the fixation of the device to the annulus of the human heart is unreliable, because the fixation of the anchor units is achieved by just pushing and/or pulling the units along the annulus, whereby the anchor units might self-secure to the tissue when being moved. Since attachment of the units to the tissue is hence unpredictable and usually does not take place in case of all of the anchor units, the device as disclosed in WO2008/088716A1 tends to disengage from the heart tissue or—even worse—detachment of the whole device with simultaneous pulling-off of parts of the heart tissue takes place, which in turn causes mitral insufficiency to persist.

Furthermore, the individual needs of a patient, which may be caused by variations in the anatomical structure of the annulus or variations in the pathological expansion pattern of the annulus, cannot be taken into account, because the device of WO2008/088716A1 causes a uniform contraction of the annulus with an equal distance reduction between the individual anchor units, which is due to the uniformly chosen distances between the anchor portions of the device. The implantation of the device as disclosed in WO2008/088716A1 might hence result in a degree of contraction which is too high in one area of the annulus, and a degree of contraction which is too little in another area. Hence after implantation of the device as disclosed in WO2008/088716A1, proper heart valve functionality cannot be guaranteed.

SUMMARY OF THE INVENTION

Therefore, it is an object of the instant invention to provide an improved annuloplasty device, which provides a reliable and permanent attachment to the annulus and which takes into account the variations in the anatomical shape or variations in the pathological changed shape of the annulus, respectively, whereby the surgical approach, in which sutures are tied to reconstruct the annulus, is effectively mimicked while avoiding massive surgery.

In order to achieve said objects, the annuloplasty device according to the invention comprises at least a first and a second anchor unit, whereby the first and second anchor units are interconnected by connection means defining a distance between the first and second anchor units, further comprising pulling means for reducing the distance between the first and second anchor units so as to pull the annulus together, wherein the anchor units are arranged to be rotatable to one another around a longitudinal axis extending along the row.

By having the anchor units arranged to be rotatable one relative to the other, the anchor units, one after the other, can be rotated into a position, in which they come into engagement with the annulus, thereby successively attaching the individual units to the annulus. In particular, the anchor units may be arranged in a row within a vascular delivery device and successively be deployed from the vascular delivery device, so that the anchor units may be fixed to the annulus in a row that follows the shape of the annulus. Thereby, the anchor units each have a longitudinal axis extending along the row of units, wherein the individual anchor units are arranged to be rotatable about said longitudinal axis.

Contracting in the sense of the present invention takes place via the reduction of the distance between two anchor units, whereby the interjacent tissue is contracted.

The annuloplasty device according to the invention may alternatively be used on a tricuspid valve, preferably on a mural leaflet of a tricuspid valve.

As already mentioned above, human annuli may show different degrees of stretchability and/or different anatomical shapes. For instance, in patients with posterior wall infarction the annulus in the P3 area of the posterior leaflet is more dilated than the annulus in the P1 area. Hence, in order to provide individual adaption properties to the varying shapes of individual annuli, the connection means define a distance between the at least first and second anchor unit, wherein said distance may be adapted to the individual characteristics of the annulus.

A normal, undilated annulus shows a length of between 18-32 mm, whereby above said range, i.e. >32 mm, the annulus is classified as dilated.

For example, in the case of low dilatation of the annulus the distance between the anchor units may preferably be chosen between 1 and 2.5 mm. In the case of a major dilatation the distance may preferably be chosen between 2.5 and 4 mm. The length of the anchor units may preferably be chosen between 2 and 10 mm.

The connection means provided for interconnecting the first and second anchor units are configured to allow the desired rotation of the units relatively to one another around their longitudinal axis.

The pulling means provide for a proper pulling, i.e. a proper movement of the anchor units towards each other, which in turn results in proper contraction of the annulus in the region lying between the units. In case of a plurality of anchor units, comprising at least two pairs of anchor units, the pulling means are each arranged to exert a pulling force between the two anchor units of a pair of anchor units, wherein the pairs are connected to each other without pulling means being provided.

Since according to the invention the anchor units are arranged rotatable to one another, a reliable and permanent attachment of the annuloplasty device to the annulus is achieved. When the anchor units rotate relatively to one another the anchor means arranged on each of the first and second anchor units move towards the annulus, whereby the anchor means are enabled to dig themselves in the tissue, which significantly favors the attachment of the device to the annulus.

Preferably, the anchor units are arranged such as to be rotatable to one another around the longitudinal axis about 45-120°, preferably 80-100°. Such a rotating angle allows the anchor means that are arranged on the anchor units to rotate between a first angular position and a second angular position, wherein the anchor means are positioned out of engagement of the annulus in said first angular position and get into engagement with the annulus in said second angular position.

In order to be space-saving and to provide a reliable connection to the tissue, the pulling means and the connection means are preferably formed integrally with each other. A space-saving design is particularly advantageous for allowing proper placement of the device inside a vascular delivery device.

More preferably, the connection means are formed as springs and/or made of a shape-memory alloy, preferably Nitinol. Springs or other flexible elements that can be deformed to exert a pulling force between their connection points advantageously combine the function of pulling means and of connection means. Whereas a spring will exert a predetermined pulling force on the anchor units to which it is connected, a shape-memory alloy may be used to control the pulling force by a commanded and controlled deformation of the shape-memory material. Furthermore, said connection means also enable rotation of the anchor units to one another when being deployed from the delivery device.

The pulling means preferably comprise electro magnets and/or electro-active polymers and/or a pneumatic means and/or a vacuum chamber and/or wires, which are all capable of inducing attraction of one anchor unit to its neighboring anchor unit.

Said pulling means may be connected to a mechanical or electric command line that extends through the delivery device, such as a catheter, to an extracorporeal control device that allows a medical operator to initiate and control the pulling action exerted by the puling means. In the case of the pulling means being configured as a wire, said wire may extend through the delivery device to the extracorporeal control device, where the medical operator can pull the wire in order to contract the annulus in its region lying between the individual anchor units.

The anchor means may preferably be anything capable of properly securing the device to the heart tissue, such as needles and/or hooks and/or clips and/or staples and/or rivets, which are preferable barbed.

In order to effectively prevent the tissue from tearing and to effectively prevent the anchor units from detaching from the tissue, the anchor means preferably have a trident shape, which enables secure attachment of the anchor units to the heart tissue.

In order to enhance the attachment properties of the device even more, at least one anchor means, preferably a plurality of anchor means, is preferably arranged on each of the first and second anchor units. The more anchor means are fixed to each of the anchor units the more attachment points between the anchor units and the heart tissue are established, which results in a more reliable connection of the anchor units to the tissue.

The anchor means are preferably deployable from a first position, in which the anchor means are retracted for being arranged within a delivery device, into a second position, in which the anchor means are deployed. Since the device is implanted in the heart by the aid of e.g. a catheter, whereby the smaller the diameter of the catheter is a less invasive method for introducing the annuloplasty device in the heart, the retracted position of the anchor means helps to realize a space-saving embodiment of the device, which easily fits in the catheter. When being pushed out of said delivery device the anchor means deploy and attach to the tissue when the anchor units rotate around their longitudinal axis.

In order to provide an initial connection to the annulus and to achieve an even more reliable connection to the annulus, the distal end of the annuloplasty device preferably carries fixing means for fixing the distal end of the annuloplasty device to the annulus. Since said fixing means are attached to the distal ends of the device, their attachment to the annulus takes place prior to the deployment of the first anchor unit and hence defines the starting point for the deployment of the anchor units.

The fixing means can be attached on one and/or both end points of the annulus and/or in the middle of the annulus, which enables the device to be deployed according to the anatomical shape of the annulus.

More preferably, the fixing means are formed by clamps and/or pliers. Clamps and pliers both serve for grabbing the annulus. In the case of pliers, the tissue may additionally be penetrated, whereby an even stronger fixation of the device to the annulus is realized.

As already mentioned before, the annuloplasty device according to the invention is deployed with the aid of a delivery device.

Accordingly, in a separate aspect of the present invention, a delivery device for delivering and deploying the annuloplasty device to the annulus of the mitral valve is provided, comprising at least one flexible tube, in which the annuloplasty device is housed prior to being delivered, a guiding wire for guiding the flexible tube to the annulus and retracting means for retracting the flexible tube relative to the at least first and second anchor units of the annuloplasty device so as to successively release the anchor units from the flexible tube.

The implantation of the annuloplasty device is realized via e.g. transcatheteral delivery, whereby the flexible tube, which houses the annuloplasty device, is delivered to the implantation site in the human heart. Correct delivery of the flexible tube to the annulus is guided with the aid of a guiding wire, which is connected to the delivery device and/or the annuloplasty device and which is steerable by the means of the catheter. When the implantation site is reached the flexible tube has to be retracted, whereby the retraction is realized by the aid of retracting means, which are also steerable by the means of the catheter. Retraction of the flexible tube results in the successive release of the anchor units, which are housed in the tube, to the implantation site, where the anchor means of the anchor units successively attach to the heart tissue following the induced rotation around their longitudinal axis.

In order to achieve simultaneous attachment of the annuloplasty device to the annulus from both end points of the annulus towards its middle section or attachment to the annulus from the middle section towards both end points of the annulus, a first and a second flexible tube are preferably provided, wherein a first section of the annuloplasty device is housed in the first flexible tube and a second section of the annuloplasty device is housed in the second flexible tube prior to being delivered.

Furthermore, the flexible tube and/or the annuloplasty device may be equipped with a plurality of pushing wires, which are on their proximal end attached to a ring, which surrounds the guiding wire of the catheter and which is axially movable on the same, and on their distal end fixed to the flexible tube and/or the annuloplasty device, whereby the ring and hence the pushing wires are also steerable by the aid of the catheter. When the implantation site is reached the ring is moved towards the implantation site and the pushing wires are pushed open due to the axial movement of the ring, span in an angle of 30-100° and hence resemble the shape of the annulus before the actual implantation of the annuloplasty device takes place.

The fixation with the fixing means, which are arranged on the distal ends of the annuloplasty device, defines the starting points of the delivery as being the endpoints and/or the middle section of the annulus, which in turn helps to already define beforehand the desired attachment pattern of the device, i.e. a pattern which resembles the anatomical structure of the annulus.

Preferably, the wall of the tube, on its inner side, has a cross-sectional profile that provides a form-fit to a corresponding cross-sectional profile of the outer surface of the anchor units so as to prevent a rotation of the anchor units when being arranged within the flexible tube. Said form fit secures the anchor units in their first angular position as long as the anchor units are arranged within the tube. As the anchor units are deployed from the tube, the anchor units are released from the form fit and are free to rotate into their second angular position. Said rotation may be controlled extracorporally by suitable control means, such as control wires, or may be automatically induced by positive guiding means, such as a guiding surface, arranged within the tube that cooperates with the anchor units so as to forcibly control the rotation as a function of their longitudinal displacement. The rotation of the anchor units as they are released from the retracting tube leads to a successive attachment of the anchor means of the anchor units to the tissue along the retracting path of the tube.

In order to favor individual adaption properties of the annuloplasty device, which is housed inside the tube, and to increase the possibility of achieving a reliable attachment of the device to the tissue, the tube preferably comprises an axial extension the inner cross-sectional profile of which allows a rotation of the anchor units around the longitudinal axis about 45-120°, preferably 80-100°, wherein the cross sectional profile preferably comprises a stopping surface for limiting the rotational movement of the anchor units. Thereby rotational movement of the device can be individually adapted to the structure of the annulus such as to fit the patient's individual needs.

Furthermore, the annuloplasty device may preferably be connected to another device for mitral valve repair, such as an artificial leaflet.

BRIEF DESCRIPTION OF THE DRAWINGS

In the following the present invention will be described by some exemplary embodiments:

FIG. 1b is a top view of the embodiment as depicted in FIG. 1a;

FIG. 1a-5d show views of the delivery device with the annuloplasty device in the different stages of implantation.

DETAILED DESCRIPTION

Figure 1A:
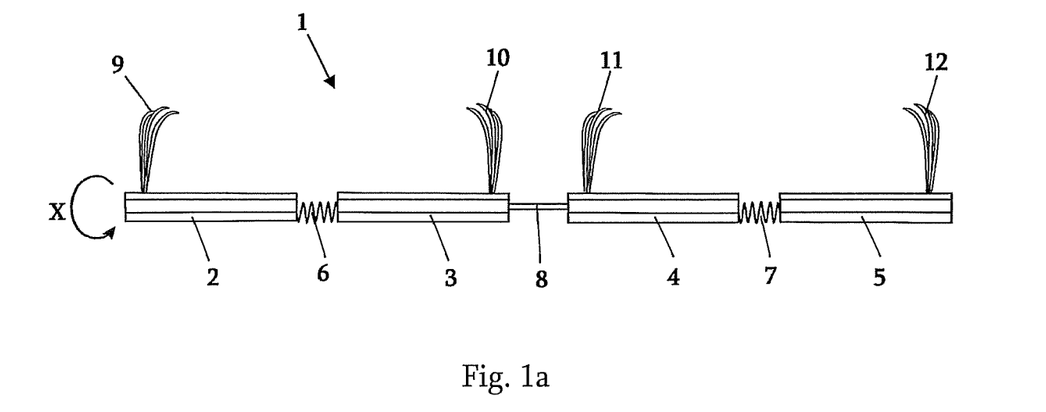
FIG. 1a is a side view of an exemplary embodiment of the annuloplasty device according to the present invention.
Figure 1B:
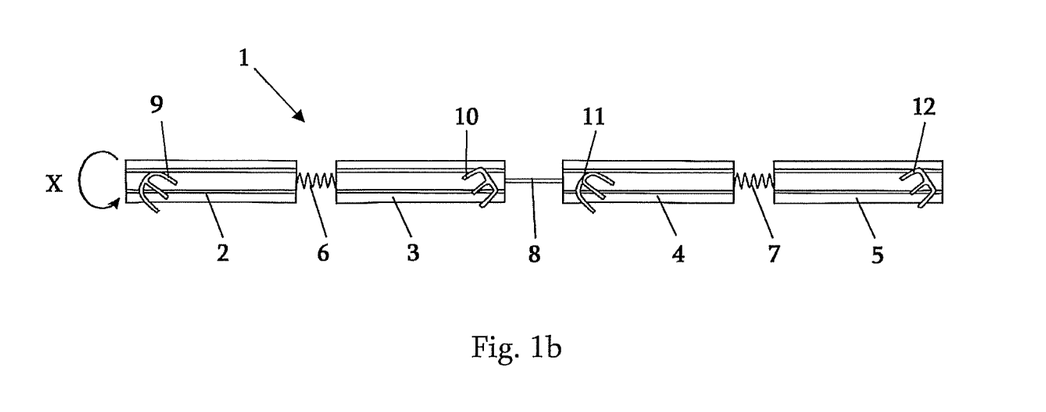

In FIG. 1a and 1b the exemplary embodiment of the annuloplasty device according to the invention is depicted with reference numeral 1. The annuloplasty device 1 comprises a first, a second, a third and a fourth anchor unit 2, 3, 4, 5, which are positioned in a row. Anchor units 2 and 3 are interconnected by spring means 6 and anchor units 4 and 5 are interconnected by spring means 7. The pair of anchor units 2, 3 is interconnected with the pair of anchor units 4, 5 via connection means 8. Each of the anchor units 2, 3, 4, 5 comprises anchor means 9, 10, 11, 12 having a trident shape, which are arranged on the end of the anchor units 2, 3, 4, 5 facing away from the springs 6, 7. The anchor units 2, 3, 4, 5 are able to rotate around their longitudinal axis according to arrow X.

Figure 2A:
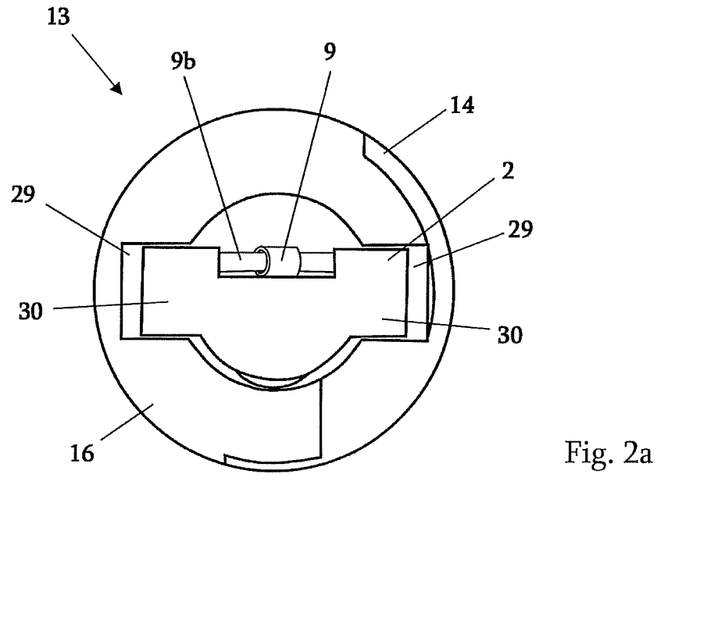
FIG. 2a-2c show a cross-sectional, a perspective and a side view of an exemplary embodiment of the delivery device according to the invention housing the annuloplasty device prior to being delivered to the heart tissue.
Figure 2B:
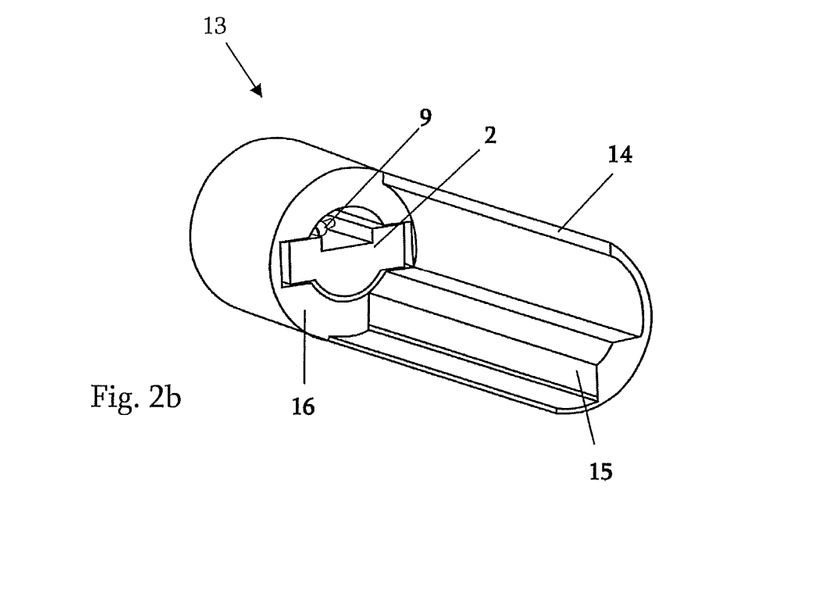
Figure 2C:
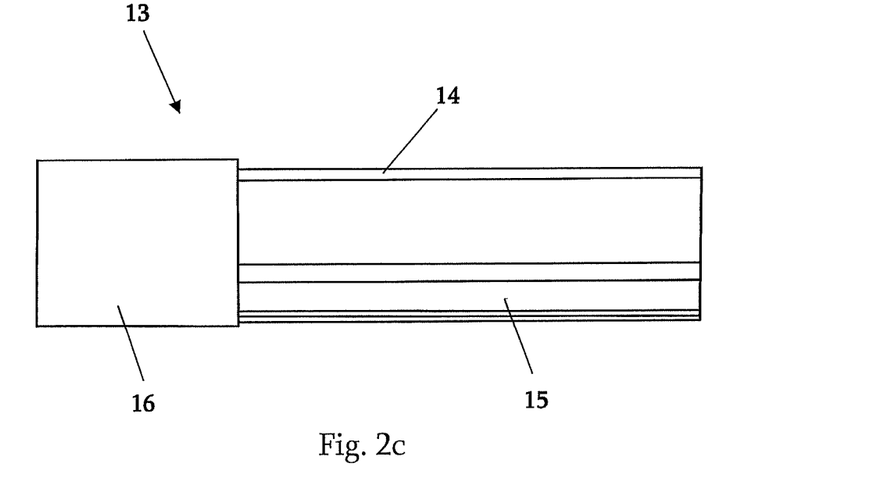

FIG. 2a shows a cross-sectional, FIG. 2b a perspective and FIG. 2c a side view of an exemplary embodiment of the flexible tube 13 of the delivery device according to the invention housing the annuloplasty device prior to being delivered to the heart tissue.

The parts, which correspond to the parts as already described with regard to FIG. 1a-1c, are designated with the same reference numerals.

In the depicted embodiment a first anchor unit 2 is shown prior to its delivery from the tube 13 of the delivery device. The anchor means 9 are fixed to the end of anchor unit 2 so as swivel around the axis 9b and are shown in their retracted position. The wall of the tube 13, on its inner side, has a cross-sectional profile that provides a form-fit to the corresponding cross-sectional profile of the outer surface of the anchor unit 2 comprising the anchor means 9 in their retracted position so as to prevent a rotation of anchor unit 2 as long as it is arranged within the flexible tube 13. In order to provide said form-fit, the tube 13 comprises two longitudinal grooves 29, in which a nose 30 of the anchor unit 2 is each guided.

Furthermore, the tube 13 comprises an extension 14, having a different inner cross-sectional profile than the tube 13 so as to allow for a rotation of the anchor unit 2 once it has left the tube 13. The extension 14 comprises a stopping surface 15, which limits the rotational movement of anchor unit 2 after its deployment (cf. FIG. 4a-4c).

Figure 3A:
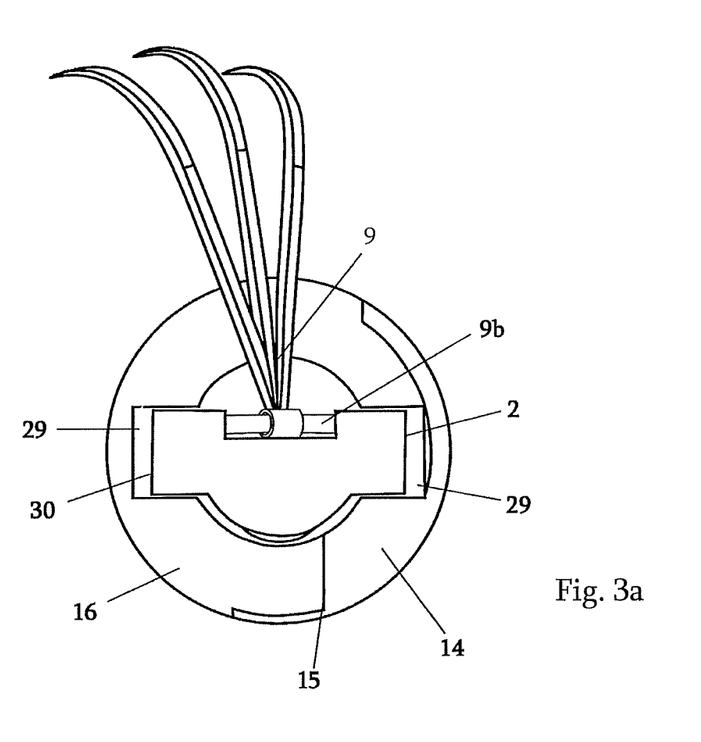
FIG. 3a-3c show a cross-sectional, a perspective and a side view of the delivery device with the first anchor unit of the annuloplasty device exiting the tube and prior to its rotation.
Figure 3B:
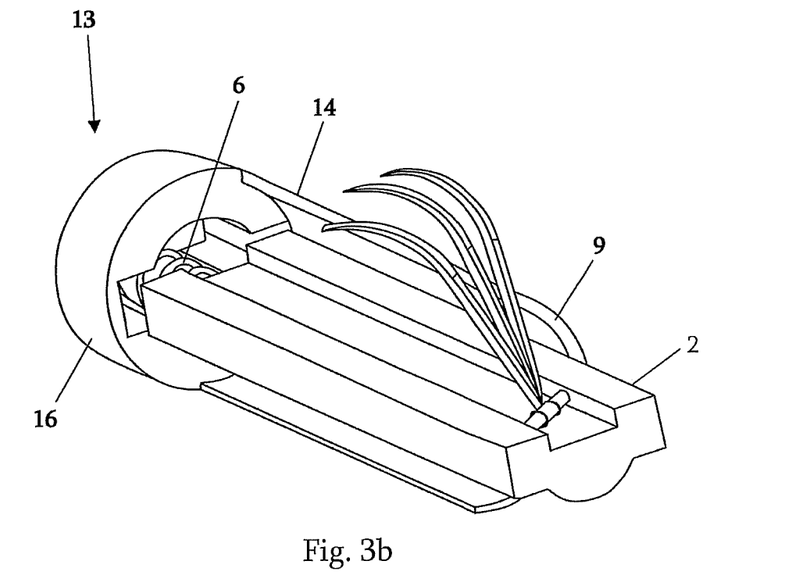
Figure 3C:
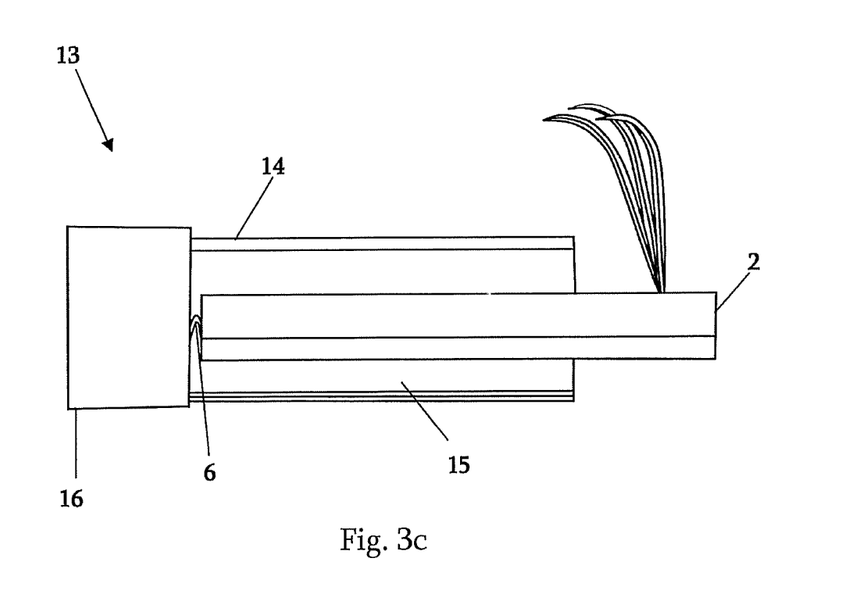

FIG. 3a shows a cross-sectional, FIG. 3b a perspective and FIG. 3c a side view of the exemplary embodiment of the flexible tube 13 of the delivery device as depicted in FIG. 2a-2c with the first anchor unit 2 of the annuloplasty device having been moved out of the tube 13 and having been arranged in the extension 14 prior to rotation. As can be taken from FIG. 3a-3c the anchor means 9 have been deployed into their second, unretracted position by a swiveling movement around the axis 9b, which takes place immediately after the whole anchor means 9 has left the form-fit profile 16 of the tube 13.

Figure 4A:
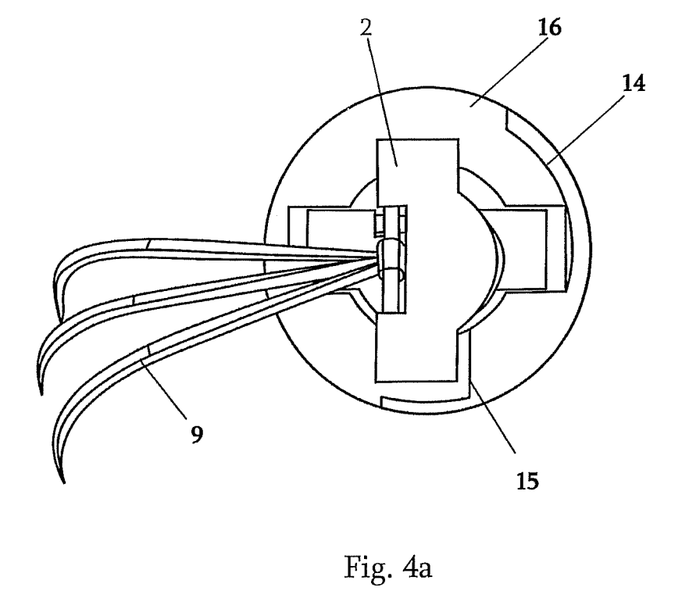
FIG. 4a-4c depict a cross-sectional, a perspective and a side view of the delivery device with the first anchor unit of the annuloplasty device in its position as in FIG. 4, but having been rotated.
Figure 4B:
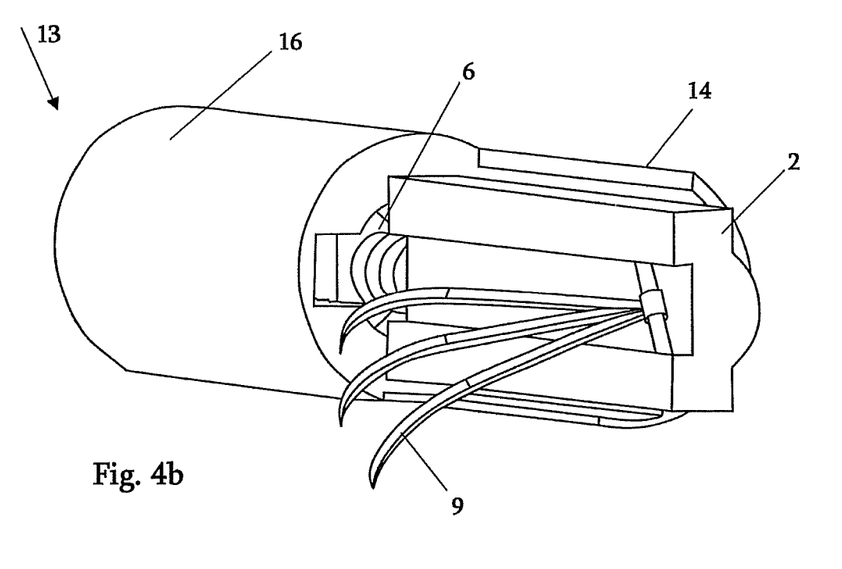
Figure 4C:
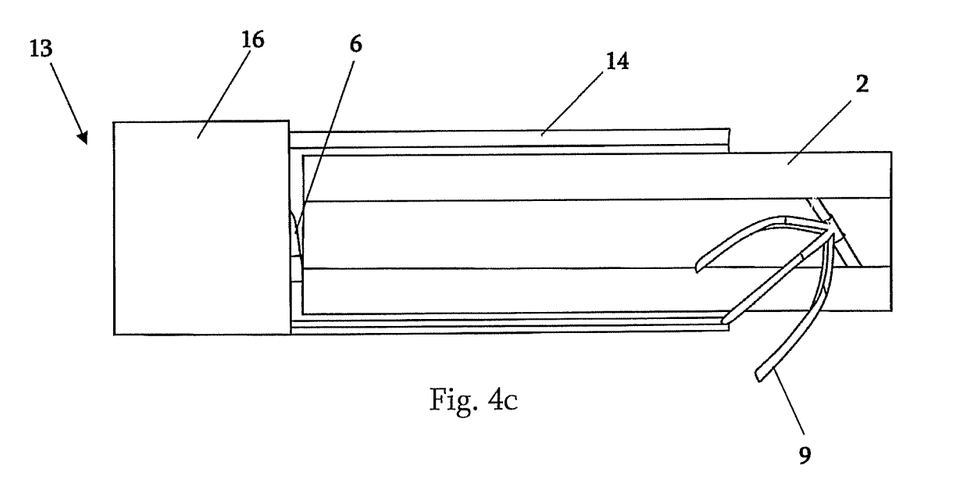

FIG. 4a depicts a cross-sectional, FIG. 4b a perspective and FIG. 4c a side view of the delivery device with the first anchor unit 2 of the annuloplasty device according to FIG. 2, but with the anchor unit 2 having been rotated. The rotation is induced via the spring means 6, which develop their rotational power after anchor unit 2 is completely delivered outside of the form-fit part 16 of the tube 13. In their rotated position as shown in FIG. 4, the anchor means 9 get into engagement with the annulus thereby fixing the anchor unit 2 to the annulus.

FIG. 5a-5d depict views of the delivery device with the annuloplasty device in the different implanting stages of the annuloplasty device. As can be taken from FIG. 5a-5d the delivery device 17 comprises a first flexible tube 13 and a second flexible tube 18, a guiding wire 29, a plurality of pushing wires 30 and a catheter sleeve 19, in which the flexible tubes 13,18, the guiding wire 29 and the pushing wires 30 were housed prior to their delivery to the position shown in FIG. 5a.

Figure 5A:
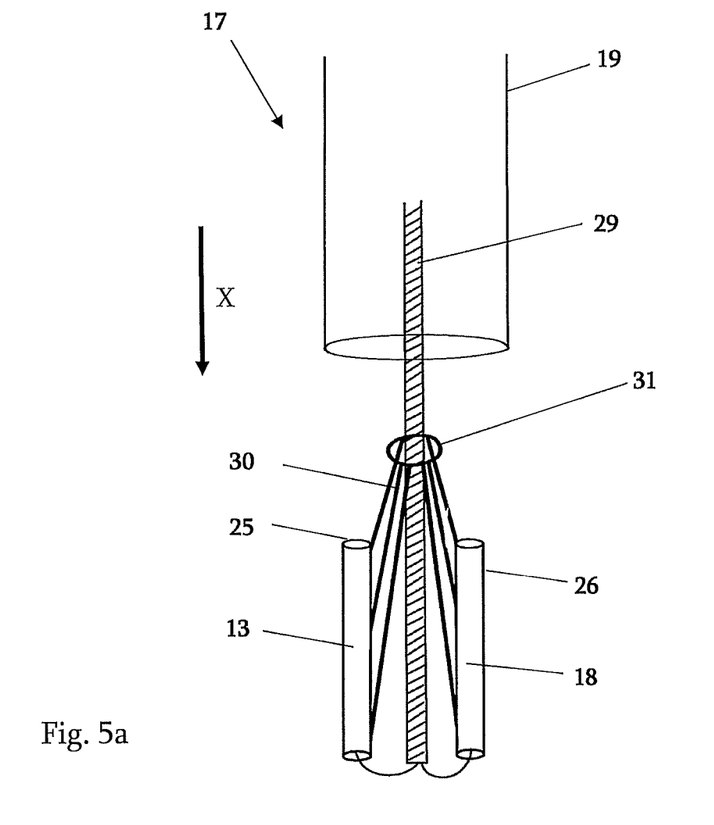
Figure 5B:
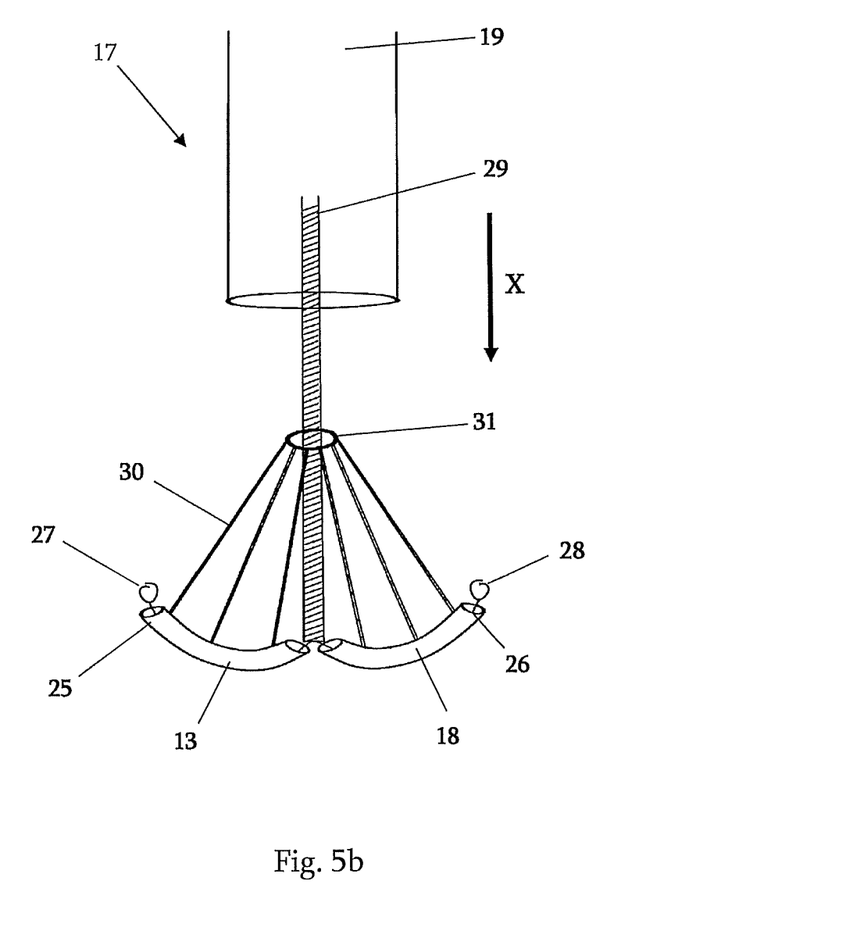

In FIG. 5a the flexible tubes 13, 18 of the delivery device 17, a part of the guiding wire 29 and the pushing wires 30 were already released from the catheter sleeve 19, whereby in FIG. 5b the flexible tubes 13, 18 already resemble the anatomical shape of the annulus, which was achieved via moving ring 31, on which the pushing wires 30 are attached on their proximal end, from the position as depicted in FIG. 5a in its axial direction according to arrow X, to the position as depicted in FIG. 5b. The axial movement of the ring 31 induces the pushing wires 30 to push open in an angle of 90°.

At the distal ends of the annuloplasty devices 1 and 20 fixing means 27, 28 are attached, which serve for fixing the distal end of the annuloplasty devices 1 and 20 to the heart tissue (not shown), whereby said fixation takes place prior to the release of the first anchor units 2 and 21, respectively.

Figure 5C:
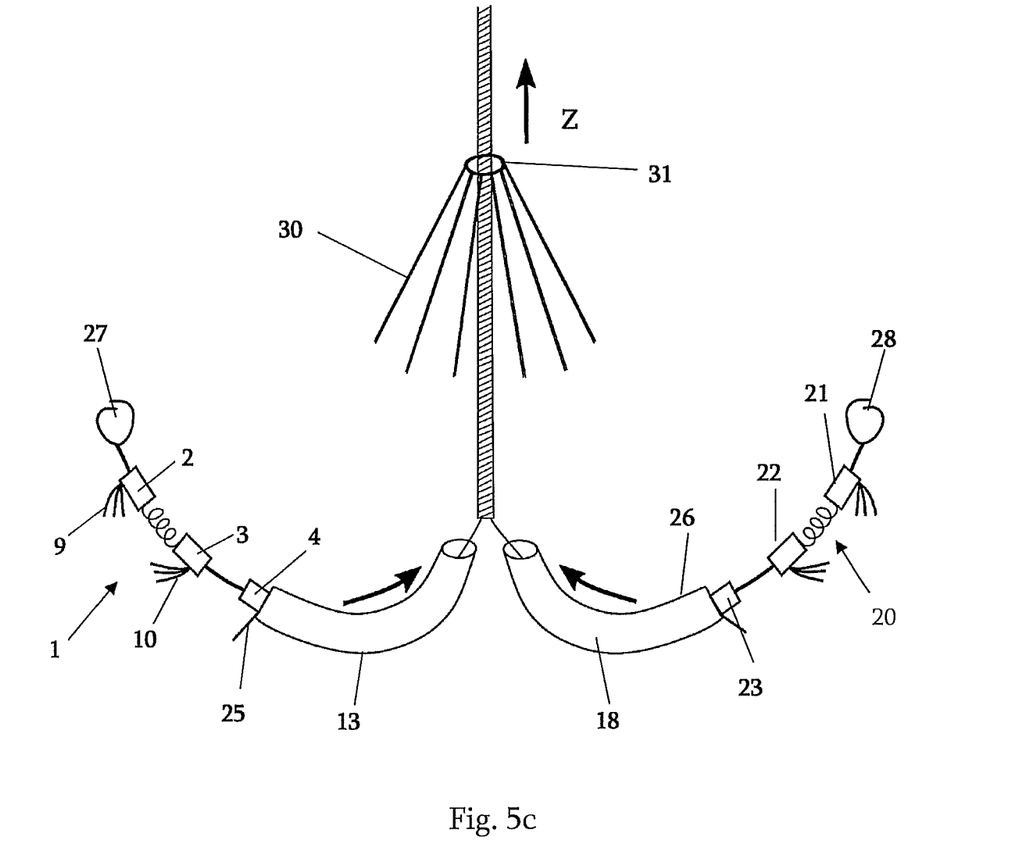

After the attachment of the fixing means 27, 28 the pusher wires 30 may be retracted from the implantation site via axially moving ring 31 in the direction of arrow Z (FIG. 5c).

Figure 5D:
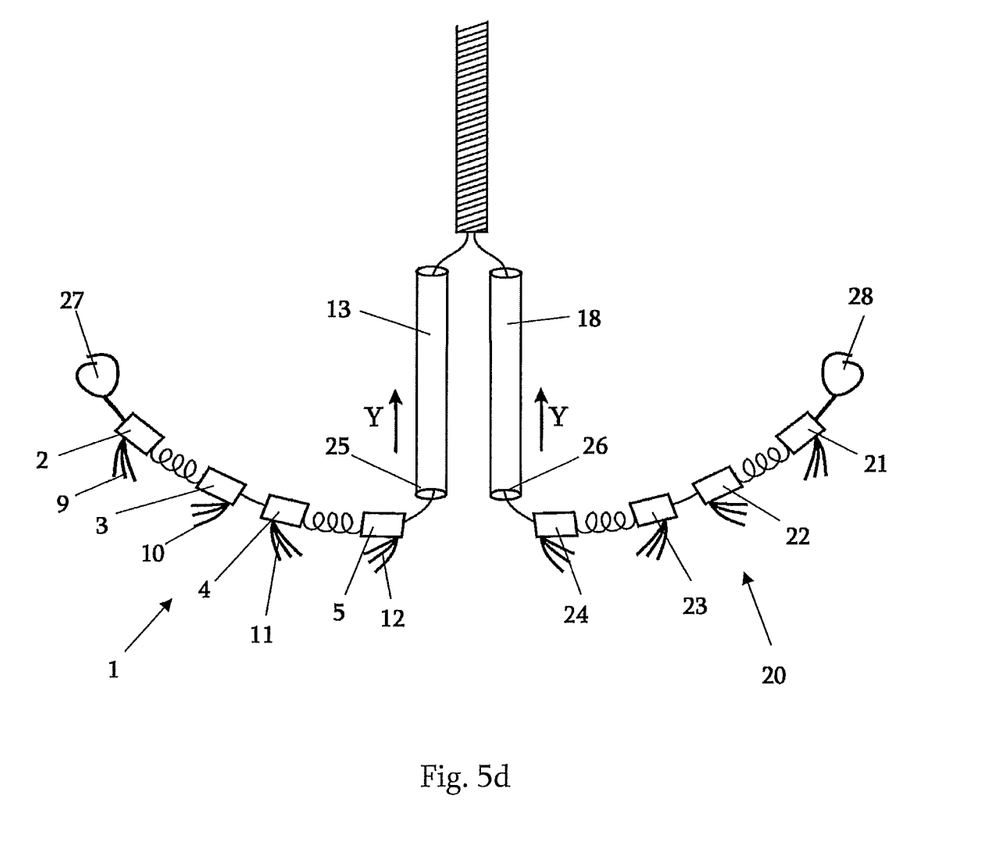

Deployment of the anchor units 2, 3, 4, 5 of the annuloplasty device 1 and anchor units 21, 22, 23, 24 of the annuloplasty device 20 starts at the free ends 25, 26 of the tubes 13, 18.

FIG. 5c shows the anchor units 2, 3 and 21, 22, which have successively been released from the tubes 13, 18, and which have already successively been rotated and are hence attached to the annulus (not shown).

FIG. 5d shows the anchor units 2, 3, 4, 5 and 21, 22, 23, 24, which have already been successively released from the tubes 13, 18, and which have already successively been rotated, whereby the anchor means 9, 10, 11, 12 on the anchor units 2, 3, 4, 5 were enabled to attach to the heart tissue (not shown).

Since the annuloplasty device as shown in FIG. 5a-5d just comprises 8 anchor units, namely anchor units 2, 3, 4, 5, 21, 22, 23, 24 FIG. 5d exhibits the full implantation state, whereby after said state is achieved tubes 13 and 18 can be removed from the implantation site via catheter sleeve 19 according to arrows Y.

The invention claimed is:

1. A delivery device with a first annuloplasty device and a second annuloplasty device, the first and second annuloplasty devices for use on a posterior annulus of a mitral valve, the delivery device for delivering and deploying the first and second annuloplasty devices to the annulus of the mitral valve, the first and second annuloplasty devices each comprising:
  at least a first and a second anchor unit that are deployable to the mitral valve by means of the delivery device and positionable in a row along the annulus, anchor means being arranged on each of the first and second anchor units;
  connection means interconnecting the first and second anchor units and defining a distance between the first and second anchor units; and
  pulling means for reducing the distance between the first and second anchor units so as to pull the annulus together;
  wherein the anchor units are arranged to be rotatable to one another around a longitudinal axis extending along the row; and
  wherein the delivery device comprises:
  a first flexible tube and a second flexible tube, the first annuloplasty device being housed in the first flexible tube and the second annuloplasty device being housed in the second flexible tube prior to being delivered, the first and second flexible tubes being for a simultaneous delivery of the first and the second annuloplasty devices;
  a guiding wire for guiding the first and second flexible tubes to the annulus; and
  retracting means for retracting the first and second flexible tubes relative to the at least first and second anchor units of the first and second annuloplasty devices, respectively, so as to successively release the anchor units from the respective flexible tube.

2. The delivery device of claim 1, wherein the delivery device comprises a catheter.

3. The delivery device of claim 1, wherein the anchor units are rotatable to one another about the longitudinal axis by 45-120 degrees.

4. The delivery device of claim 3, wherein the anchor units are rotatable to one another about the longitudinal axis by 80-100 degrees.

5. The delivery device of claim 1, wherein:
the pulling means and the connection means are formed integrally with each other; and
the connection means are at least one of formed as springs and made of a shape-memory alloy.

6. The delivery device of claim 5, wherein the connection means are made of Nitinol.

7. The delivery device of claim 1, wherein the pulling means comprise at least one of electro magnets, electro-active polymers, a pneumatic means, a vacuum chamber, wires, and rigid wires.

8. The delivery device of claim 1, wherein the anchor means comprise at least one of needles, hooks, clips, staples, and rivets.

9. The delivery device of claim 1, wherein a plurality of anchor means are arranged on each of the first and second anchor units.

10. The delivery device of claim 1, wherein the anchor means are deployable from a first position, in which the anchor means are retracted for being arranged within the vascular delivery device, into a second position, in which the anchor means are deployed.

11. The delivery device of claim 1, wherein a distal end of the annuloplasty device carries fixing means for fixing the distal end of the annuloplasty device to the annulus.

12. An annuloplasty device, for use on a posterior annulus of a mitral valve, comprising:
at least a first and a second anchor unit that are deployable to the mitral valve by means of a vascular delivery device and positionable in a row along the annulus, anchor means being arranged on each of the first and second anchor units;
connection means interconnecting the first and second anchor units and defining a distance between the first and second anchor units; and
pulling means for reducing the distance between the first and second anchor units so as to pull the annulus together;
wherein the anchor units are arranged to be rotatable to one another around a longitudinal axis extending along the row; and
wherein the anchor means have a trident shape.

13. An annuloplasty device, for use on a posterior annulus of a mitral valve, comprising:
at least a first and a second anchor unit that are deployable to the mitral valve by means of a vascular delivery device and positionable in a row along the annulus, anchor means being arranged on each of the first and second anchor units;
connection means interconnecting the first and second anchor units and defining a distance between the first and second anchor units; and
pulling means for reducing the distance between the first and second anchor units so as to pull the annulus together;
wherein the anchor units are arranged to be rotatable to one another around a longitudinal axis extending along the row;
wherein a distal end of the annuloplasty device carries fixing means for fixing the distal end of the annuloplasty device to the annulus; and
wherein the fixing means are formed by at least one of clamps and pliers.

14. A delivery device with an annuloplasty device, the annuloplasty device for use on a posterior annulus of a mitral valve, the delivery device for delivering and deploying the annuloplasty device to the annulus of the mitral valve, the annuloplasty device comprising:
at least a first and a second anchor unit that are deployable to the mitral valve by means of the delivery device and positionable in a row along the annulus, anchor means being arranged on each of the first and second anchor units;
connection means interconnecting the first and second anchor units and defining a distance between the first and second anchor units; and
pulling means for reducing the distance between the first and second anchor units so as to pull the annulus together;
wherein the anchor units are arranged to be rotatable to one another around a longitudinal axis extending along the row; and
wherein the delivery device comprises:
at least one flexible tube, in which the annuloplasty device is housed prior to being delivered;
a guiding wire for guiding the flexible tube to the annulus; and
retracting means for retracting the flexible tube relative to the at least first and second anchor units of the annuloplasty device so as to successively release the anchor units from the flexible tube;
wherein a wall of the tube, on its inner side, has a cross-sectional profile that provides a form-fit to a corresponding cross-sectional profile of an outer surface of the anchor units so as to prevent a rotation of the anchor units within the flexible tube.

15. The delivery device of claim 14, wherein:
the tube comprises an axial extension of the inner cross-sectional profile which allows a rotation of the anchor units about the longitudinal axis by 45-120 degrees; and
the cross sectional profile comprises a stopping surface for limiting the rotational movement of the anchor units.

16. The delivery device of claim 15, wherein the tube comprises the axial extension of the inner cross-sectional profile which allows the rotation of the anchor units about the longitudinal axis by 80-100 degrees.

* * * * *